(12) United States Patent
Lober (10) Patent No.: US 12,178,661 B2
(45) Date of Patent: Dec. 31, 2024

(54) MEDICAL HAND GUARD

(71) Applicant: Stephen Bruce Lober, Athens, GA (US)

(72) Inventor: Stephen Bruce Lober, Athens, GA (US)

( * ) Notice: Subject to any disclaimer, the term of this patent is extended or adjusted under 35 U.S.C. 154(b) by 775 days.

(21) Appl. No.: 17/215,774

(22) Filed: Mar. 29, 2021

(65) Prior Publication Data

US 2021/0298861 A1    Sep. 30, 2021

Related U.S. Application Data

(60) Provisional application No. 63/000,854, filed on Mar. 27, 2020.

(51) Int. Cl.
| | | |
|---|---|---|
| *A61B 90/00* | (2016.01) | |
| *A41D 13/08* | (2006.01) | |
| *A61B 17/00* | (2006.01) | |

(52) U.S. Cl.
CPC ............ *A61B 90/04* (2016.02); *A41D 13/081* (2013.01); *A41D 13/087* (2013.01); *A61B 2017/00438* (2013.01); *A61B 2017/00876* (2013.01); *A61B 2017/00889* (2013.01); *A61B 2090/0436* (2016.02)

(58) Field of Classification Search
CPC .... A41D 13/081; A41D 13/087; A41D 13/08; A41D 19/002; A41D 19/01; A41D 19/015; A41D 27/20; A47L 13/16; A47L 13/18; A61F 13/105
USPC ...... 2/16, 20, 21, 158, 159, 161, 161.6, 163, 2/161.7, 161.8, 164
See application file for complete search history.

(56) References Cited

U.S. PATENT DOCUMENTS

| | | | | |
|---|---|---|---|---|
| 3,141,216 A | * | 7/1964 | Haskell | A41F 1/002 24/303 |
| 3,407,927 A | * | 10/1968 | Stephen | A47G 21/001 294/1.3 |
| 5,832,540 A | * | 11/1998 | Knight | A41D 27/20 2/244 |
| 6,145,128 A | * | 11/2000 | Suzuki | A41D 13/087 2/21 |
| 2004/0172735 A1 | * | 9/2004 | Garland | A41D 19/0041 2/160 |
| 2005/0114983 A1 | * | 6/2005 | Demay | A41D 19/01529 2/160 |
| 2013/0007987 A1 | * | 1/2013 | Kleindorfer | B25G 1/102 16/431 |
| 2014/0028039 A1 | * | 1/2014 | Rampersad | A61F 13/105 294/99.2 |
| 2014/0068828 A1 | * | 3/2014 | Holmes | A41D 13/087 2/21 |

FOREIGN PATENT DOCUMENTS

| | | | | |
|---|---|---|---|---|
| DE | 202010013670 U1 | * | 1/2011 | ........... A61F 13/105 |
| GB | 2496649 A | * | 5/2013 | ........... A41D 13/087 |
| KR | 100478775 B1 | * | 3/2005 | ......... A41D 19/0006 |

* cited by examiner

*Primary Examiner* — Aiying Zhao
(74) *Attorney, Agent, or Firm* — Ballard Spahr LLP (57) ABSTRACT

A medical hand guard that serve as a protective barrier between a user's hand and potentially contaminated surfaces is disclosed. The medical band guard can comprise a base pad and first and second pockets that are configured to receive a respective thumb and finger of the user. The medical hand guard can define a contact surface opposite the first and second pockets.

11 Claims, 12 Drawing Sheets

MEDICAL HAND GUARD

CROSS-REFERENCE TO RELATED APPLICATION

This application claims priority to and the benefit of the filing date of U.S. Provisional Patent Application No. 63/000,854, filed Mar. 27, 2020, the entirety of which is hereby incorporated by reference herein.

FIELD

This application relates to medical hand guards and, in particular, to medical hand guards that provide a barrier between the hands of health care workers and potentially contaminated surfaces.

BACKGROUND

Pathogens capable of causing disease usually enter our bodies through the eyes, mouth, nose, urogenital openings, or breaches in the skin barrier. These pathogens can be transmitted by a number of routes, including 1) direct contact with a contaminated surface, 2) via airborne droplet transmission, 3) via contaminated food, water, and blood, and 4) by way of intervening vectors (fleas, mosquitos, ticks, etc.), influenza and COVID-19 viruses can be spread by airborne droplet transmission, but are also commonly spread by indirect contact with contaminated surfaces (fomites) such as door handles, elevator buttons, faucet handles, and counter tops, among many others. The average health care worker comes into contact with such surfaces hundreds of times during the course of a normal eight hour work day. Avoidance of contact with higher risk surfaces can markedly reduce the rate of transmission of pathogens to health care workers in the hospital or other medical setting.

SUMMARY

Described herein, in various aspects, is a medical hand guard. In exemplary configurations, the medical hand guard can include a base pad, a contact surface secured to or defined by a first side of the base pad, and first and second pockets positioned on an opposing second side of the base pad. The contact surface can include metal ion-impregnated, antimicrobial fabric that is designed to minimize pathogenic accumulation on the contact surface. The base pad can define the basic form of the device and provide an additional barrier between the user's hand and the contact surface. The pockets can define the spaces for receiving the index (or middle) finger and the thumb of a health care worker, while allowing the user to grasp, pull, and push potentially contaminated surfaces. Optionally, the hand guard can be attached or coupled to a retractable holder, that itself can be attached to a lab coat pocket or other item worn by or associated with the health care worker.

In one aspect, an apparatus can be used providing a barrier for a hand of a user, the hand having a thumb and a finger. The apparatus can have a first end and a second end spaced along a longitudinal axis. The apparatus can comprise a base pad having a first side and an opposing second side. A first pocket can be disposed on the first end of the apparatus, wherein the first pocket is configured to receive at least a portion of the thumb of the user. The first pocket can define a first opening on the first side of the base pad. The first opening can be spaced from the first end of the apparatus in a first direction from the first end of the apparatus toward the second end of the apparatus. A second pocket can be disposed on the second end of the apparatus, wherein the second pocket is configured to receive at least a portion of the finger of the user. The second pocket can define a second opening on the first side of the base pad. The second opening can be spaced from the second end of the apparatus in a second direction that is opposite the first direction. The apparatus can define a contact surface on a side of the apparatus opposing the first side of the base pad.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE DRAWINGS

These and other features of the preferred embodiments of the invention will become more apparent in the detailed description in which reference is made to the appended drawings wherein:

FIGS. 10A-10B depict the deployment of a medical hand guard as disclosed herein.

DETAILED DESCRIPTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout. It is to be understood that this invention is not limited to the particular methodology and protocols described, as such may vary. It is also to be understood that the terminology used herein is for the purpose of describing particular embodiments only, and is not intended to limit the scope of the present invention.

Many modifications and other embodiments of the invention set forth herein will come to mind to one skilled in the art to which the invention pertains having the benefit of the teachings presented in the foregoing description and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

As used herein the singular forms "a," "an," and "the" include plural referents unless the context clearly dictates otherwise. For example, use of the term "a magnet" can refer to one or more of such magnets, and so forth.

All technical and scientific terms used herein have the same meaning as commonly understood to one of ordinary skill in the art to which this invention belongs unless clearly indicated otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Optionally, in some aspects, when values are approximated by use of the antecedent "about," it is contemplated that values within up to 15%, up to 10%, up to 5%, or up to 1% (above or below) of the particularly stated value can be included within the scope of those aspects. Similarly, in some optional aspects, when values are approximated by use of the terms "substantially" or "generally," it is contemplated that values within up to 15%, up to 10%, up to 5%, or up to 1% (above or below) of the particular value can be included within the scope of those aspects. When used with respect to an identified property or circumstance, "substantially" or "generally" can refer to a degree of deviation that is sufficiently small so as to not measurably detract from the identified property or circumstance, and the exact degree of deviation allowable may in some cases depend on the specific context.

As used herein, the terms "optional" or "optionally" mean that the subsequently described event or circumstance may or may not occur, and that the description includes instances where said event or circumstance occurs and instances where it does not.

As used herein, the term "at least one of" is intended to be synonymous with "one or more of." For example, "at least one of A, B and C" explicitly includes only A, only B, only C, and combinations of each.

The word "or" as used herein means any one member of a particular list and also includes any combination of members of that list.

As described herein, a magnetic material should be understood to include both one or more magnets and a material that is configured to magnetize in the presence of a magnet to thereby cause a magnetic attraction to said magnet. In various optional aspects, the magnet(s) can comprise one or more rare earth magnets, one or more ferrite magnets, one or more flexible magnets, or any other suitable magnet type (e.g., permanent magnets). The magnetic material that is configured to magnetize in the presence of a magnet can include, for example, a ferromagnetic material.

It is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; and the number or type of aspects described in the specification.

The following description supplies specific details in order to provide a thorough understanding. Nevertheless, the skilled artisan would understand that the apparatus, system, and associated methods of using the apparatus can be implemented and used without employing these specific details. Indeed, the apparatus, system, and associated methods can be placed into practice by modifying the illustrated apparatus, system, and associated methods and can be used in conjunction with any other apparatus and techniques conventionally used in the industry.

Disclosed herein, in various aspects and with reference to FIGS. 1A-10B, is a medical hand guard. In use, the medical hand guard can serve as a protective barrier between an individual's hand and any potentially contaminated surface. The medical hand guard can be particularly well suited for individuals in a medical environment, such as, for example, healthcare workers.

Figure 10A:
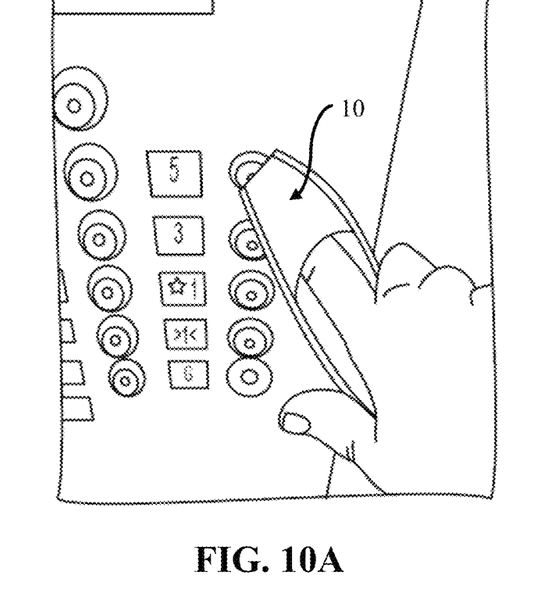
FIG. 10A depicts the hand guard during "no touch" pushing of elevator buttons.
Figure 10B:
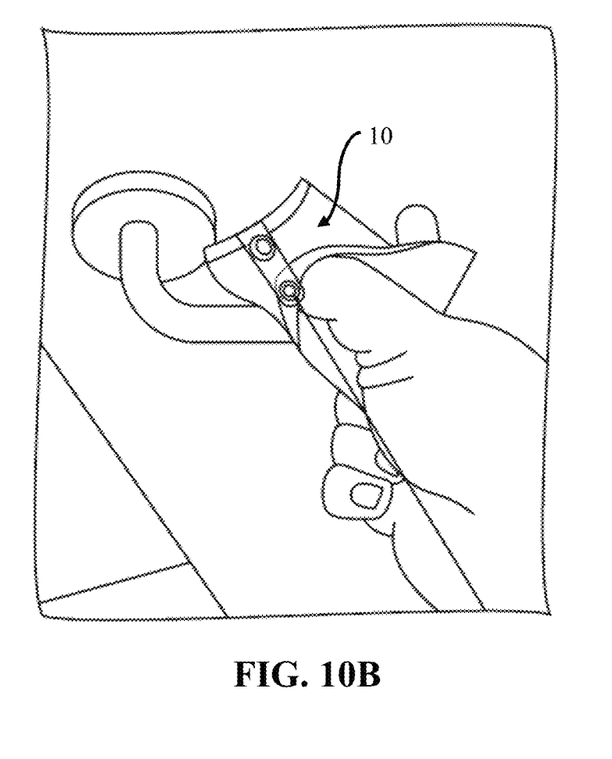
FIG. 10B depicts the hand guard during "no touch" grasping of a door handle.

The hand guard can include a base pad equipped with individual pockets for insertion of the index (or middle) finger and the thumb of the health care worker. As shown in FIGS. 10A-B, the pockets can allow the hand guard to be used as a "partial glove." That is, the pockets can define the spaces for receiving the index (or middle) finger and the thumb of the health care worker, while allowing the user to grasp, pull, and push potentially contaminated surfaces such as door knobs or handles (FIG. 10B), automatic door pressure pads, drawer pulls, and elevator buttons (FIG. 10A), among many others. Thus, the hand guard can be used when opening door handles, pushing elevator buttons or automatic door pressure pads, opening drawers, or turning faucets, thereby preventing direct contact with contaminated surfaces. In use, it is contemplated that the pockets can allow for tactile pushing and grasping by the health care worker without the health care worker coming into direct contact with potentially contaminated surfaces. It is contemplated that the hand guard disclosed herein can more quickly and easily be donned on the hand and removed from the hand than a conventional glove. Moreover, hand guard can be reusable, unlike conventional medical gloves, leading to less waste. The base pad can comprise or be made of any natural or synthetic fabric, any silicone material, or any disposable paper product or material. It is further contemplated that the base pad can be made in multiple configurations, shapes, and/or sizes, and in any and all colors available for the manufacture of the above-listed materials.

In some aspects, a hand guard 10 can have a longitudinal axis 12. The hand guard 10 can have first and second ends 16, 18 that are spaced along the longitudinal axis 12. The hand guard 10 can comprise a base pad 20 having a first side 22 and an opposing second side 24. The hand guard 10 can have a first pocket 30 at the first end 16 of the hand guard and a second pocket 32 at the second end 18 of the hand guard. The first pocket 30 can be configured to receive a thumb of the individual, and the second pocket 32 can be configured to receive a finger (e.g., an index or middle finger) of the individual. The first pocket 30 can define a first opening 34 that is spaced from the first end 16 of the hand guard in a first direction 36 (from the first end of the apparatus toward the second end of the apparatus). The second pocket 32 can define a second opening 38 that is spaced from the second end 18 of the hand guard in a second direction 40 (opposite the first direction 36). The base pad 20 can comprise or be made of any natural or synthetic fabric, any silicone material, or any disposable paper product or material.

Figure 2:
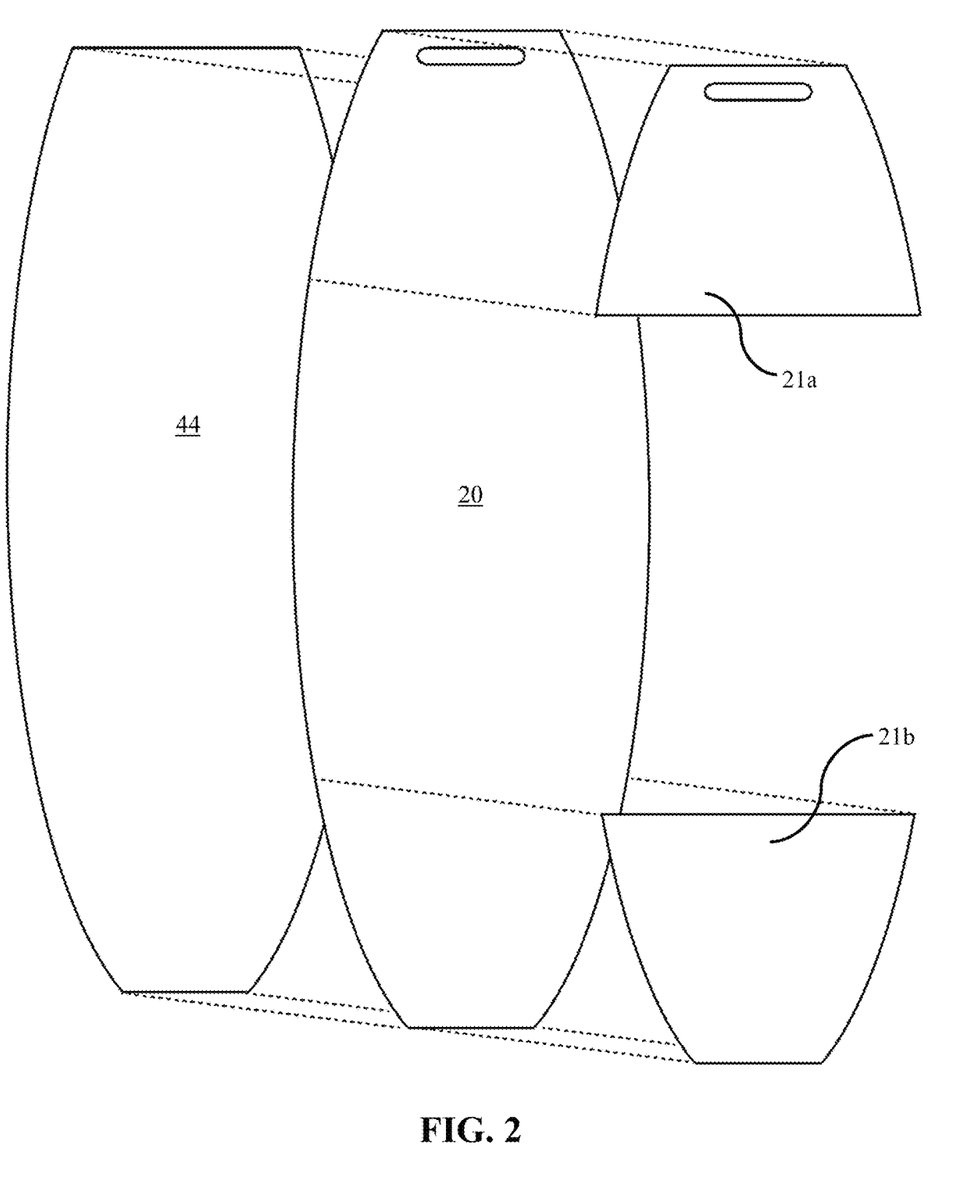
FIG. 2 is an exploded perspective view of an exemplary medical hand guard as disclosed herein.
Figure 6:
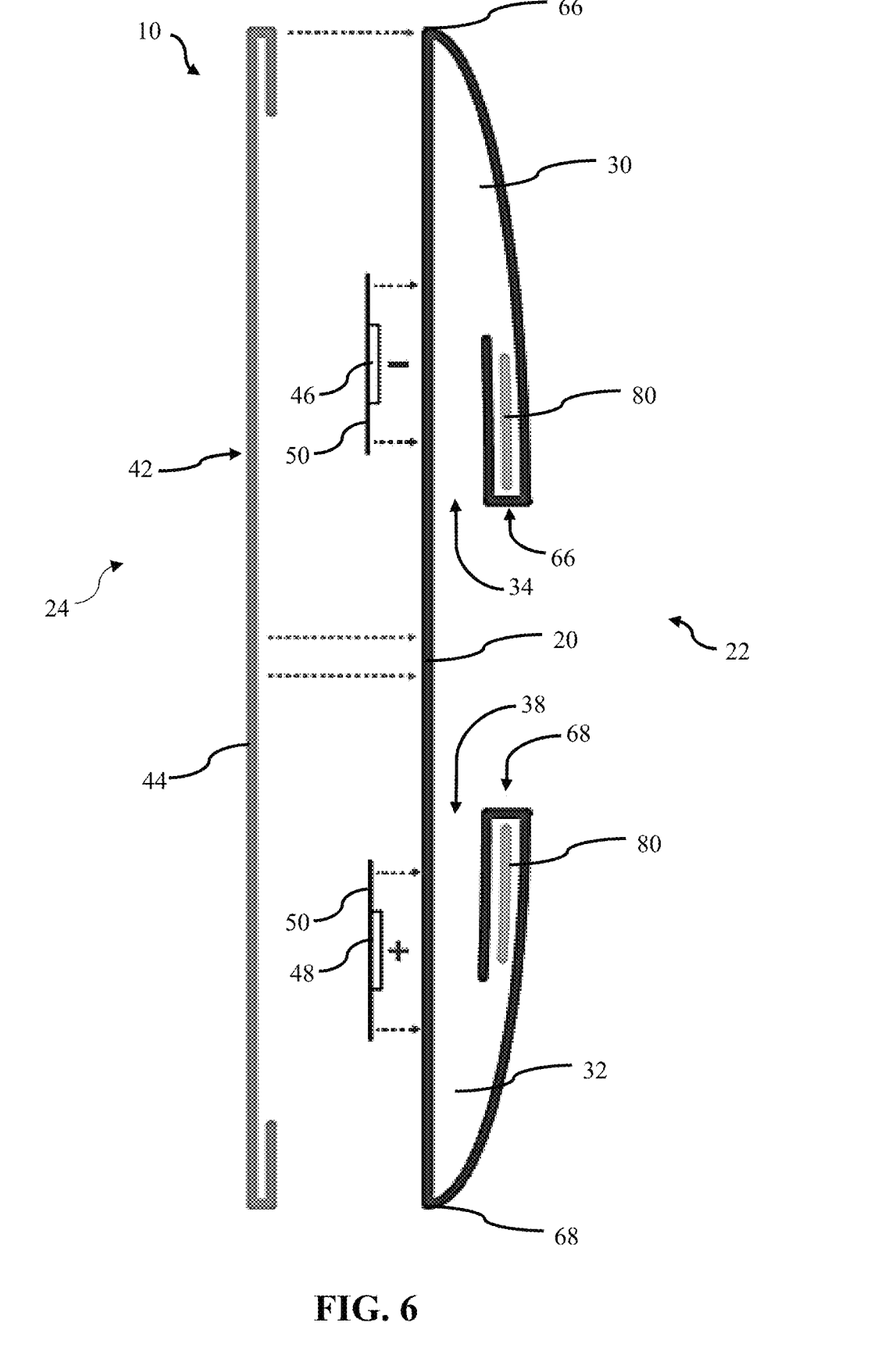
FIG. 6 is an exploded side view of an exemplary medical hand guard as disclosed herein.
Figure 7:
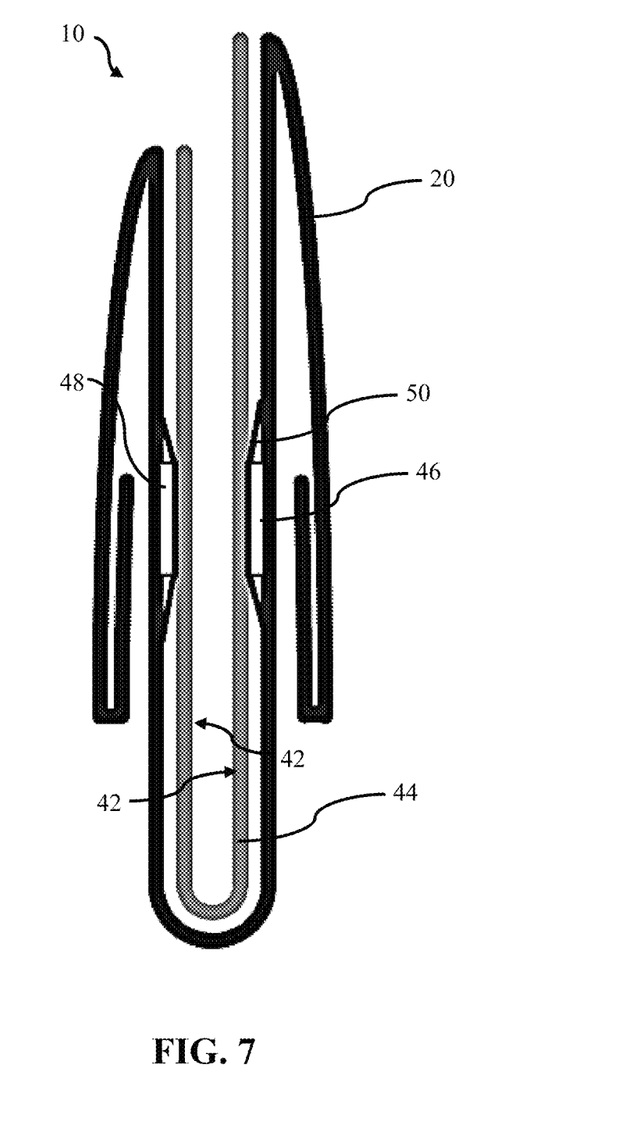
FIG. 7 is a side view of the medical hand guard of FIG. 5 in a fully folded position.

Optionally, in exemplary aspects, the second side 24 of the base pad 20 can define a contact surface 42 (that is configured to directly contact contaminated surfaces (e.g., fomite surfaces) during use of the hand guard). In further aspects, at least one contact layer 44 can be coupled to second side 24 of the base pad 20, and the contact layer 44 can define the contact surface 42. For example, stitching 45 (FIG. 9) about at least a portion of a perimeter of the base pad can couple the contact layer(s) to the base pad. In these aspects, the contact layer(s) 44 can comprise one or more layers of anti-microbial fabric that is configured to minimize the build-up of potential pathogens on the contact surface. In exemplary aspects, the anti-microbial fabric of the contact layer can be any metallic (silver; copper; zinc; etc.) ion-impregnated fabric that has been shown to inhibit pathogenic growth and transmission. As shown in FIGS. 2 and 6, the pockets of the hand guard can be positioned on an opposite side of the base pad from the contact surface.

Figure 3:
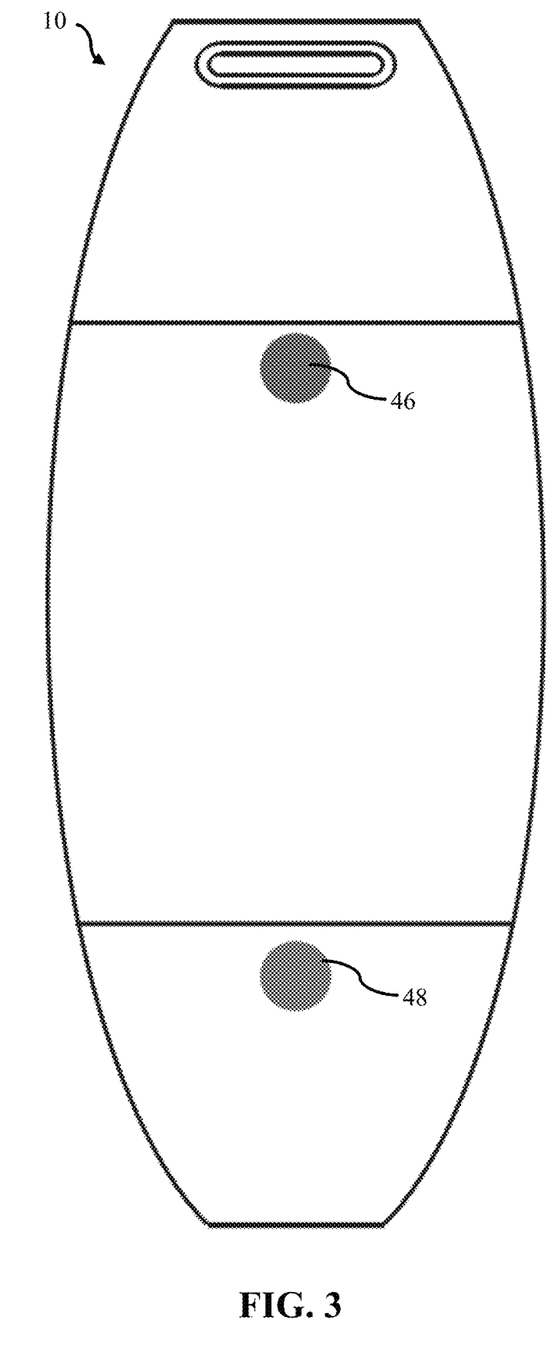
FIG. 3 is a front elevational view of an exemplary medical hand guard as disclosed herein, depicting optional locations of magnetic components as further described herein.
Figure 4A:
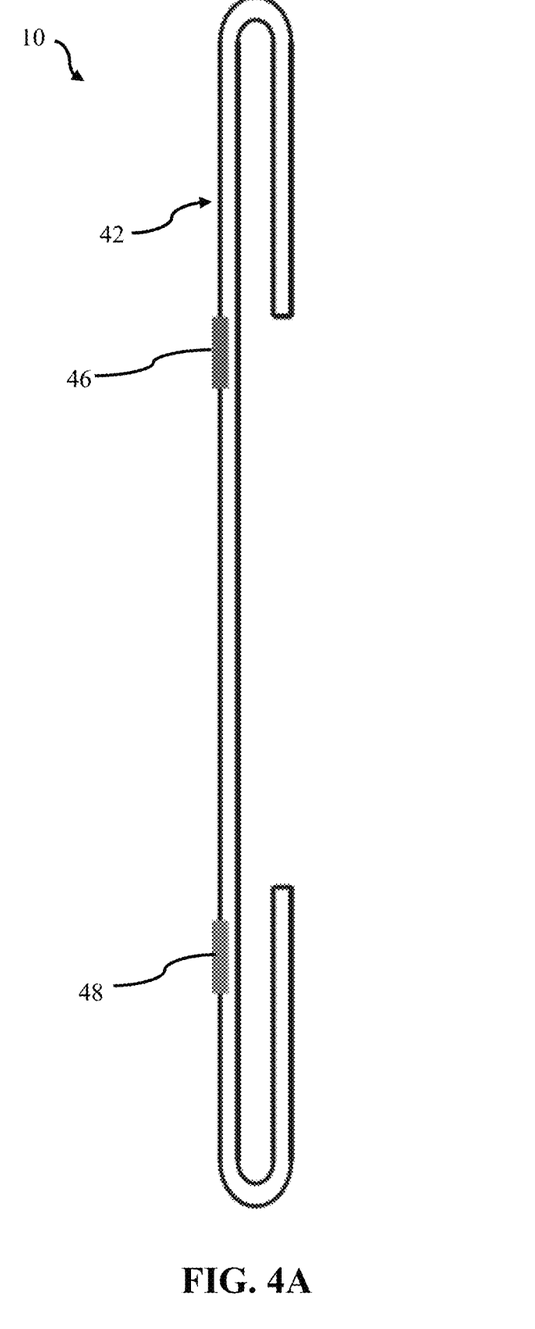
FIG. 4A depicts the medical hand guard of FIG. 3 in a fully unfolded "use" position.
Figure 4B:
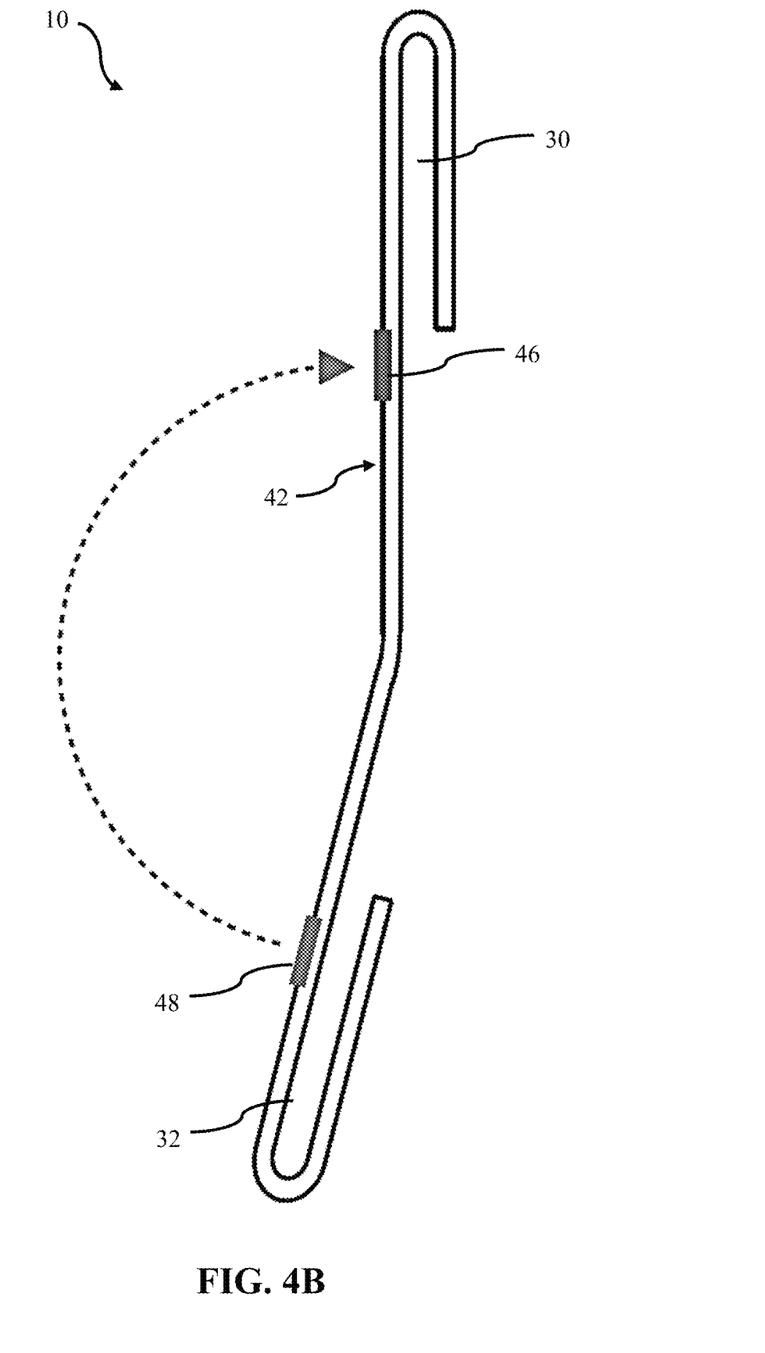
FIG. 4B depicts the folding of the medical hand guard of FIG. 4A.
Figure 4C:
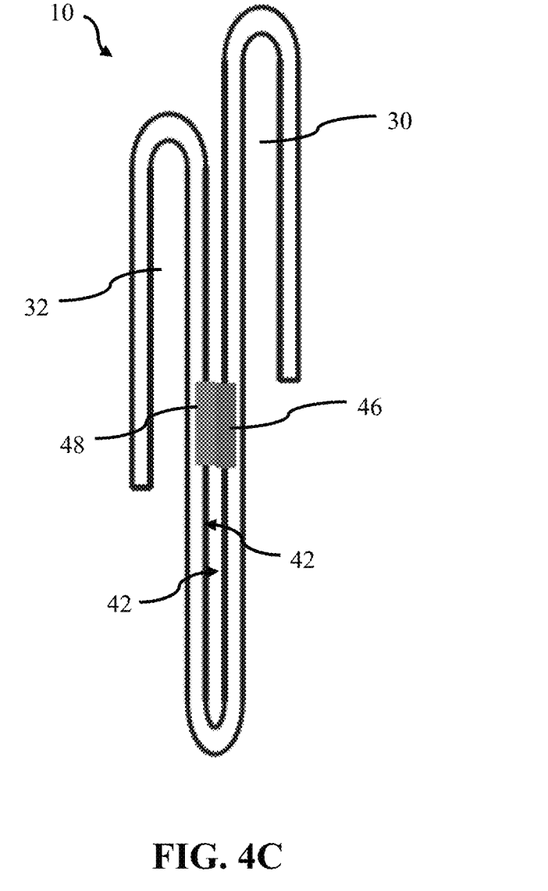
FIG. 4C depicts the medical hand guard of FIG. 4A in a fully folded position.
Figure 5:
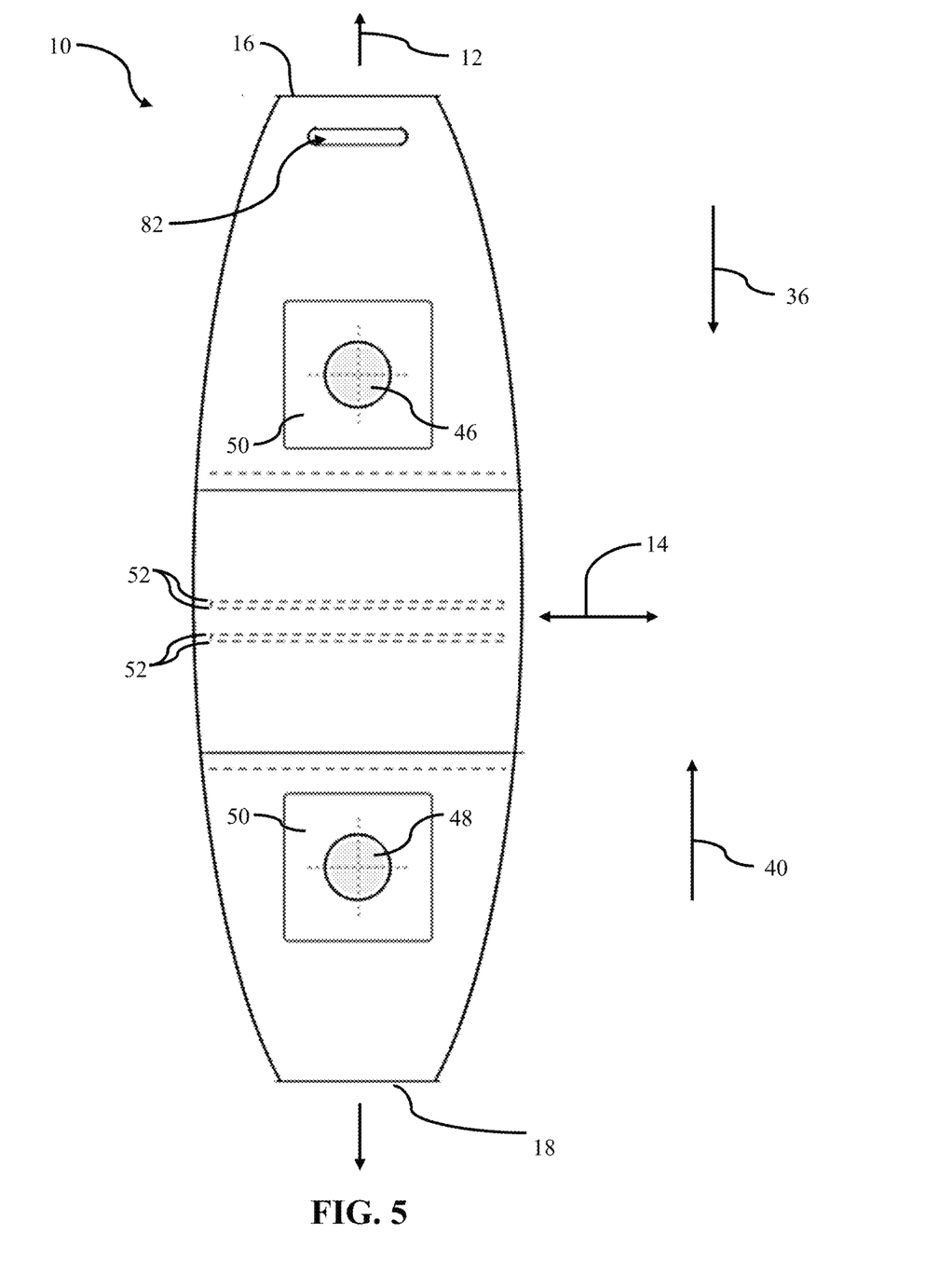
FIG. 5 is a front elevational view of an exemplary medical hand guard as disclosed herein.

Optionally, in exemplary aspects, and as shown in FIGS. 3-4C and 5-6, the hand guard 10 can be folded about a folding axis 14 so that the contact surface 42 of the hand guard folds up into itself (so that no or substantially no portion of the contact surface faces outwardly), thereby minimizing exposure of the contact surface to the health care worker's clothing or other objects or dust/aerosol particles in the environment. The base pad 20 can comprise at least one embedded magnet that is configured to retain the base pad in a folded configuration. In further aspects, other fasteners can be used in addition to or as an alternative to magnets. For example, hook and loop material, a snap element, or other, suitable fasteners can selectively retain the base pad in the folded configuration. More particularly, as shown in FIGS. 3, 5, and 6, the embedded magnet(s) can comprise first and second magnets 46,48 spaced apart along the longitudinal axis of the hand guard when the hand guard is in an unfolded, fully extended "use" configuration. The first magnet 46 can be spaced from the folding axis 14 by a distance (e.g., optionally, between 1.5 inches and 2 inches, about 1.75 inches, or 1.75 inches) in the second direction. The second magnet 48 can be spaced from the folding axis 14 by the same distance in the first direction so that, when the hand guard 10 is folded about the folding axis, the first and second magnets 46,48 can engage with their polar axes coaxially aligned (or substantially aligned). The first and second magnets 46,48 can be positioned between the two pockets of the hand guard, with the first magnet positioned proximate the first pocket 30, and the second magnet positioned proximate the second pocket 32. When the hand guard 10 is folded up from a fully extended "use" configuration, one of the magnets can approach the other magnet until magnetic polar attraction is established between the two magnets and the hand guard is retained in a folded/closed position. It is contemplated that the two magnets can be embedded in an orientation that ensures establishment of polar attraction between the two magnets when the hand guard 10 is folded up from the use configuration. The first and second magnets 46, 48 can optionally be disc magnets. The first and second magnets 46, 48 can optionally be rare earth magnets. The first and second magnets 46, 48 can each be embedded within the base pad 20 by forming a bond between a respective attachment sheet 50 and the base pad with the respective magnet positioned between and enclosed within the attachment sheet and the base pad. In further aspects, one of the first magnet or the second magnet can be replaced with a magnetic material that is configured to magnetize in the presence of a magnetic field (e.g., a ferrous metal washer or disc). Accordingly, said magnetic material can be magnetized in the presence of the magnet to form a magnetic coupling therebetween.

In various aspects, the folding axis 14 can be unequally spaced between the first and second ends 16, 18 of the hand guard 10. For example, in some optional aspects, the folding axis 16 can spaced from the first end 16 by a distance that is greater than distance from the folding axis to the second end 18 by at least one quarter inch. In further optional aspects, the folding axis can be equally spaced between the first and second ends 16, 18 of the hand guard 10.

Optionally, the hand guard 10 can comprise at least one series of stitches 52 that are proximate to, and extend parallel to, the folding axis 14. For example, as shown, the hand guard can comprise two pairs of two series of stitches 52 that are positioned on opposing sides of the folding axis 14. The series of stitches 52 can promote folding of the hand guard and be configured to couple the base pad 20 and the contact layer 44 together at the fold to inhibit separation between the base pad 20 and the contact layer 44. The series of stitches 52 can also serve to minimize or eliminate spacing between opposing sides of the contact surface when in the folded configuration.

In some optional aspects, as shown in FIG. 2, the first and second pockets can be formed via a first element that is coupled (e.g., stitched) to another element. For example, in one specific, exemplary embodiment, the hand guard 10 can have three separate layers. The contact layer 44, representing the first layer, can comprise metal ion-impregnated, antimicrobial fabric that is designed to minimize pathogenic accumulation on the contact surface. The base pad 20, representing the second layer, can define the basic form of the device and provide an additional barrier between the user's hand and the contact surface. The pocket portions 21a,b, representing the third layer, can cooperate with the base layer to define the spaces for receiving the index (or middle) finger and the thumb of the health care worker.

Figure 8:
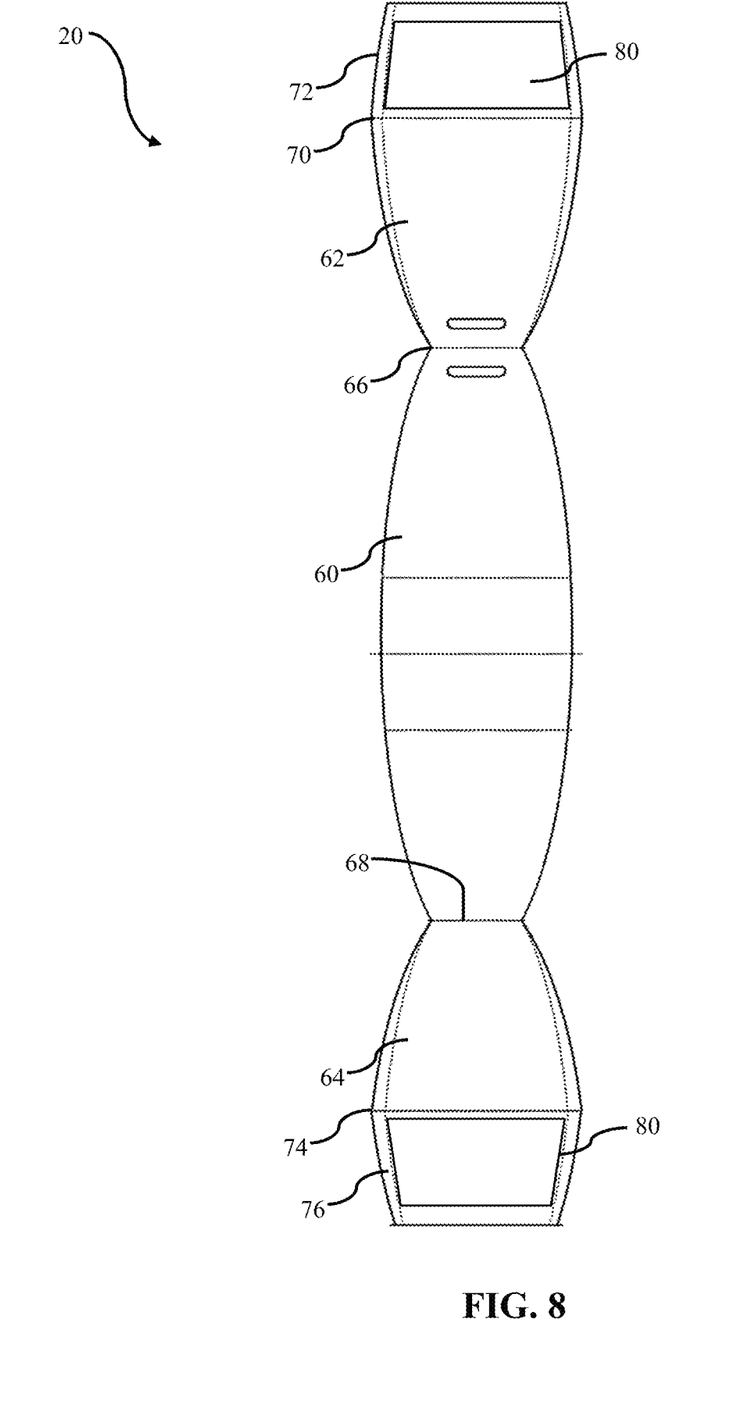
FIG. 8 depicts a profile of a base pad of an exemplary medical hand guard in accordance with embodiments disclosed herein, wherein the base pad is in an unfolded configuration prior to assembly of the medical hand guard.
Figure 9:
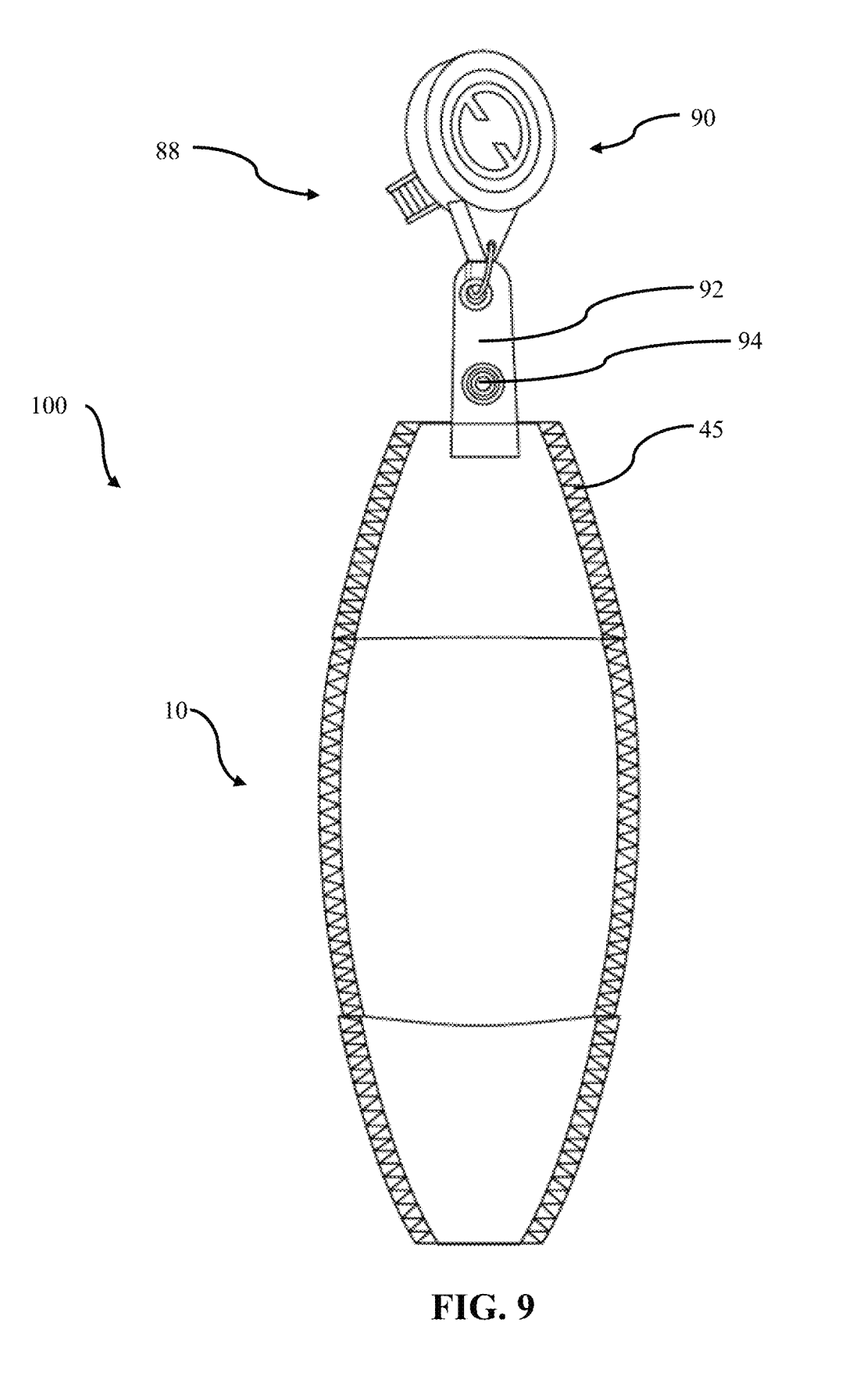
FIG. 9 depicts an apparatus including a medical hand guard that is coupled to a retractable holder as disclosed herein.

In further aspects, with reference to FIGS. 6 and 8, the first and second pockets 30, 32 can be formed from a folded sheet of material that includes the base pad 20. For example, the base pad 20 can have a main body portion 60, a first pocket portion 62, and a second pocket portion 64. The base pad 20 can define a first fold 66 between the main body portion 60 and the first pocket portion 62. The base pad 20 and first pocket portion 62 can cooperate to define the first pocket 30. The base pad 20 can define a second fold 68 between the main body portion 60 and the second pocket portion 64. The base pad 20 and second pocket portion 64 can cooperate to define the second pocket 32. Accordingly, in some aspects, the first told 66 can define the first end 16 of the hand guard 10, and the second fold 68 can define the second end 18 of the hand guard. In this way, the second end 18 of the apparatus can be devoid of stitches that could inhibit tactile sensation (e.g., when pressing buttons, as illustrated in FIG. 10A).

The base pad 20 can define a third fold 70 across the first pocket portion 62 so that a portion 72 of the base pad can be folded into and received within the first pocket 30. The base pad 20 can define a fourth fold 74 across the second pocket portion 64 so that a portion 76 of the base pad can be folded into and received within the first pocket 30. Accordingly, the third fold 70 can at least partially define the first opening 34, and the fourth fold 72 can at least partially define the second opening 38.

In some optional aspects, the first and second pockets 30, 32 can comprise respective stiffening elements 80. The stiffening elements 80 can reinforce the pockets to stabilize the pocket material or otherwise add a degree of rigidity and/or resilience. For example, the stiffening element 80 can inhibit the openings of the pockets from collapsing, thereby allowing the user to easily insert her finger and thumb. The stiffening elements 80 can extend at least partially across the respective first or second pocket 30, 32. Optionally, as shown in FIG. 6, the stiffening elements 80 can be disposed between folded portions of the first and second pocket portions 62, 64. In some optional aspects, the stiffening element 80 can comprise, for example, a fabric stiffener/stabilizer provided by PELLON (e.g., PELLON 75 fabric stiffener).

Optionally, it is contemplated that at least one end portion of the hand guard can comprise an engagement portion that is configured to permit selective engagement between the hand guard and a pocket or other structure to securely couple the hand guard to clothing of a health care worker. The engagement portion can comprise a clip, clamp, carabineer, hook, or other suitable device for removably securing the hand guard to the clothing, belt, or other garment of the health care worker.

Optionally, as shown in FIGS. 3, 5, and 8, the hand guard 10 can comprise a coupling feature that is configured to permit coupling or attachment of the hand guard to a retractable holder 88, which can be attached to a lab coat pocket (or any other garment), a belt, etc. As is known in the art, such retractable holders 88 can include a selectively retractable or deployable tether 90. Such retractable holders 88 are well-known and commonly used for holding identification badges and keycards. Accordingly, in some aspects, the retractable holder 88 can be of the conventional type used with work badges. The retractable holder 88 can comprise a looped strip of material 92 and a fastener 94 (e.g., a snap fastener) that is configured to secure the looped material to itself. The retractable holder can further comprise a spool that rotationally biases the tether toward a retracted configuration. In further aspects, a non-retractable holder, such as a lanyard, can be used with the hand guard.

Optionally, as shown in FIGS. 1 and 5, the coupling feature can comprise an opening 82 positioned at an end (e.g., at the first end 16, outward of the first pocket 30) of the hand guard. The opening 82 can be elongate in a dimension transverse to the longitudinal axis 12 of the hand guard 10. For example, the opening 82 can optionally have a length of about ¾ inches and a width of about ⅛ inch (or any suitable dimensions for coupling to the retractable holder). The opening 82 can optionally be spaced from the first end by less than ½ inch, or about ¼ inch. The opening 82 can receive the looped strip of material of the retractable holder 88. In some aspects, a grommet 84 can be positioned at an end of the hand guard. The grommet 84 can optionally comprise stainless steel. In further aspects, the grommet 84 can comprise another metal, or polymer. Alternative coupling features include fasteners, such as, for example, snaps, pins, hook-and-loop attachments, slots, retaining rings, clamps, clasps, clips, screws, bolts, and the like.

In this example, the cable/tether of the retractable holder 88 can be coupled or secured to the coupling feature of the hand guard 10 to form an assembly 100. In use, the retractable holder can permit rapid deployment of the hand guard, followed by rapid, automatic and self-contained retrieval/retraction. This deployment and retraction process can avoid the need for removing the hand guard from within a pocket, or the need for placing the hand guard back within a pocket, thereby helping to avoid inadvertent contamination of the health care worker's hand (by, for example, contact with the contact surface of the device). In this way, direct contact with high traffic hospital surfaces is markedly reduced.

The hand guard 10 can be topically cleaned with alcohol or other disinfectants. The hand guard can be machine washed. It is further contemplated that the hand guard can be sterilized via steam autoclave as needed. It is further contemplated that the hand guard can be decontaminated using ultra-violet (UV) light.

Figure 1A:
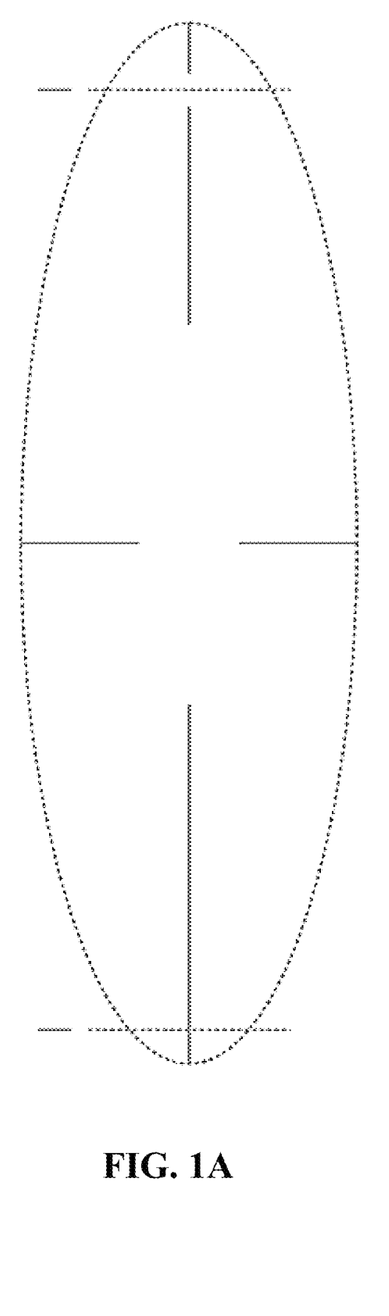
FIG. 1A depicts an exemplary elliptical profile that can be used to define a portion of the periphery of a medical hand guard as disclosed herein.
Figure 1B:
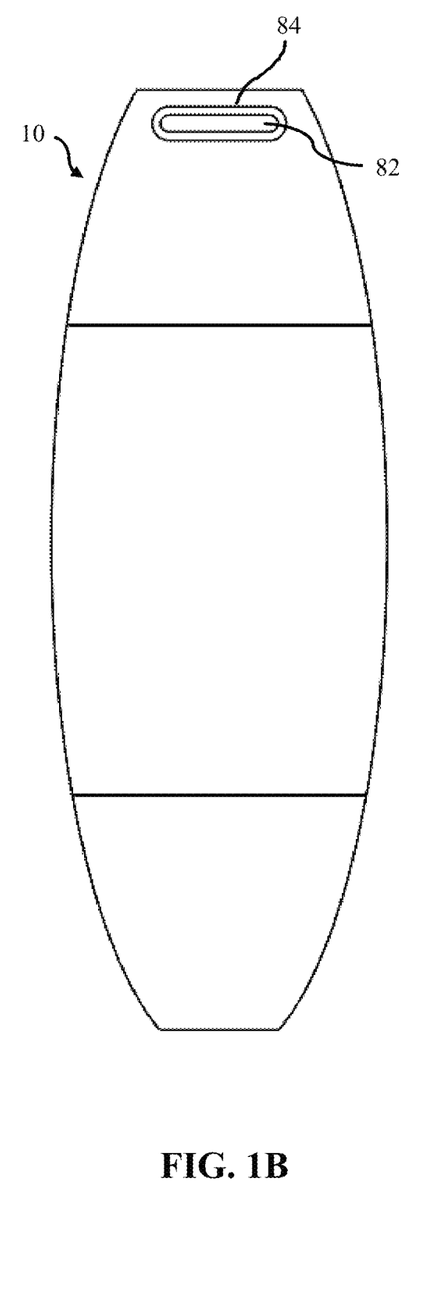
FIG. 1B is a front elevational view of an exemplary medical hand guard as disclosed herein. As shown, the hand guard can have a periphery that is partially defined by the elliptical profile of FIG. 1A.

As stated herein, the hand guard can be provided in various dimensions. In some optional aspects, the hand guard 10 can have a length along the longitudinal axis 12 of between 6 and 9 inches, or about 7 inches, or about 7.5 inches. In some optional aspects, the first opening 34 can be spaced from the first end 16 of the hand guard 10 by from about 1 inch to about 3.5 inches (e.g., about 1.75 inches to about 3 inches). In some optional aspects, the second opening 38 can be spaced from the second end 18 by from about 1 one inch to about three inches, (e.g., from about 1.75 inches to about 2.5 inches). Accordingly, each of the first and second pockets 30, 32 can have a respective depth of between 1 inch and 3 inches. In some optional aspects, the hand guard 10 can have longitudinally extending sides, wherein the longitudinally extending sides trace portions of an ellipse 26 (FIG. 1A). In some optional aspects, the hand guard can have a maximum width (in a dimension parallel to the folding axis 14) of between 2 and 3 inches, or about 2.5 inches. In some optional aspects, the width of the first and second ends 16, 18 can be narrower than the maximum width. For example, the width at the first and second ends can be between about ⅞ inch and about 1.25 inches.

Although the foregoing invention has been described in some detail by way of illustration and example for purposes of clarity of understanding, certain changes and modifications may be practiced within the scope of the appended claims.

What is claimed is:

1. An assembly comprising:
   an apparatus for providing a barrier for a hand of a user, the hand having a thumb and a finger, the apparatus having a first end and a second end spaced along a longitudinal axis, the apparatus comprising:
   a base pad having a first side and an opposite second side;
   a first pocket on the first end of the apparatus, wherein the first pocket is configured to receive at least a portion of the thumb of the user, wherein the first pocket defines a first opening on the first side of the base pad, wherein the first opening is spaced from the first end of the apparatus in a first direction from the first end of the apparatus toward the second end of the apparatus, and a second pocket on the second end of the apparatus, wherein the second pocket is configured to receive at least a portion of the finger of the user, wherein the second pocket defines a second opening on the first side of the base pad, wherein the second opening is spaced from the second end of the apparatus in a second direction that is opposite the first direction, wherein the apparatus defines a contact surface on a side of the apparatus opposite the first side of the base pad, and wherein the apparatus defines an aperture therethrough; and a holder comprising a tether that is coupled to the first end of the apparatus, wherein the holder defines a looped material strip and a fastener that is configured to secure a first portion of the looped material strip to a second portion of the looped material strip, wherein the looped material strip is inserted through the aperture of the apparatus and encircles the first end of the apparatus.

2. The assembly of claim 1, wherein the tether is retractable.

3. The assembly of claim 1, wherein the apparatus comprises a contact material coupled to or defined by the second side of the base pad, wherein the contact material comprises a metal ion-impregnated, antimicrobial fabric, wherein the contact material defines the contact surface of the apparatus.

4. The assembly of claim 3, wherein the second side of the base pad defines the contact surface.

5. The assembly of claim 1, wherein the apparatus has a folding axis that is transverse to the longitudinal axis, wherein the apparatus comprises:

a first magnet that is spaced from the folding axis in the second direction by a distance; and a magnetic material that is spaced from the folding axis in the first direction by the distance, wherein the magnetic material is configured to be magnetically attracted to the first magnet.

6. The assembly of claim 5, wherein the magnetic material is a second magnet that is oriented to have an opposing polarity of the first magnet when the apparatus is folded about the folding axis so that the second magnet is brought into proximity with the first magnet.

7. The assembly of claim 1, wherein the base pad has a main body portion, a first pocket portion and a second pocket portion, wherein the base pad defines a first fold between the main body portion and the first pocket portion so that the main body portion and first pocket portion cooperate to define the first pocket, and wherein the base pad defines a second fold between the main body portion and the second pocket portion so that the main body portion and second pocket portion cooperate to define the second pocket.

8. The assembly of claim 7, wherein the first fold defines the first end of the apparatus, and wherein the second fold defines the second end of the apparatus.

9. The assembly of claim 1, wherein the apparatus further comprises a respective stiffening element that extends across at least a portion of each of the first pocket and the second pocket.

10. The assembly of claim 1, wherein the apparatus has a perimeter having longitudinally extending sides, wherein the longitudinally extending sides each have a respective curvature corresponding to respective portions of an ellipse.

11. The assembly of claim 1, wherein the apparatus further comprises a grommet positioned within the aperture, wherein the aperture is an elongate aperture.

\* \* \* \* \*